United States Patent
Potta et al.

(10) Patent No.: US 9,662,334 B2
(45) Date of Patent: *May 30, 2017

(54) SILDENAFIL SUBLINGUAL SPRAY FORMULATIONS

(71) Applicant: Insys Development Company, Inc., Chandler, AZ (US)

(72) Inventors: Thrimoorthy Potta, Phoenix, AZ (US); Kiran Amancha, Chandler, AZ (US); Wesley Giron, Phoenix, AZ (US); Ningxing Yan, Chandler, AZ (US); Venkat Goskonda, Phoenix, AZ (US); Onkar N. Singh, Chandler, AZ (US)

(73) Assignee: INSYS DEVELOPMENT COMPANY, INC., Chandler, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/089,490

(22) Filed: Apr. 2, 2016

(65) Prior Publication Data

US 2016/0287593 A1 Oct. 6, 2016

Related U.S. Application Data

(60) Provisional application No. 62/142,746, filed on Apr. 3, 2015.

(51) Int. Cl.
| | |
|---|---|
| *A61K 47/10* | (2006.01) |
| *A61K 31/519* | (2006.01) |
| *A61K 9/00* | (2006.01) |
| *A61K 47/12* | (2006.01) |
| *A61K 47/02* | (2006.01) |

(52) U.S. Cl.
CPC ............ *A61K 31/519* (2013.01); *A61K 9/006* (2013.01); *A61K 47/10* (2013.01); *A61K 47/12* (2013.01); *A61K 47/02* (2013.01)

(58) Field of Classification Search
USPC .................. 514/329, 252.16, 262.1
See application file for complete search history.

(56) References Cited

U.S. PATENT DOCUMENTS

| | | | |
|---|---|---|---|
| 9,370,518 B2 * | 6/2016 | Amancha | A61K 9/006 |
| 2013/0143894 A1* | 6/2013 | Bergstrom | A61K 31/519 |
| | | | 514/252.16 |

FOREIGN PATENT DOCUMENTS

| | | |
|---|---|---|
| WO | 0205820 A1 | 1/2002 |
| WO | 2012103039 A1 | 2/2012 |
| WO | 2013085904 A1 | 6/2013 |

OTHER PUBLICATIONS

Hassan; Expert Opinion on Drug Delivery; 2010, 7(1), 97-112.*

* cited by examiner

*Primary Examiner* — Pancham Bakshi (74) *Attorney, Agent, or Firm* — Wood, Phillips, Katz, Clark & Mortimer (57) ABSTRACT

The invention is directed to sublingual spray formulations containing sildenafil. The invention is further directed to methods of treating male sexual dysfunction or pulmonary arterial hypertension by administering sublingual spray formulations containing sildenafil to patients in need of such treatments.

19 Claims, 1 Drawing Sheet

SILDENAFIL SUBLINGUAL SPRAY FORMULATIONS

FIELD OF THE INVENTION

The invention is directed to sublingual spray formulations containing sildenafil. The invention is further directed to methods for treating male erectile dysfunction or pulmonary arterial hypertension by administering sublingual spray formulations containing sildenafil to patients in need of such treatments.

BACKGROUND OF THE INVENTION

Sildenafil is a selective inhibitor of cyclic guanosine monophosphate (cGMP)-specific phosphodiesterase type 5 (PDE5). PDE5 is the predominant isozyme that metabolizes cGMP formed in the corpus cavernosum. Sildenafil is thought to enhance the effect of nitric oxide due to its inhibitory effect in the corpus cavernosum. The enhanced effect of nitric oxide therefore increases the cavernosal blood flow in the penis and lungs.

Sildenafil citrate is commercially available as a film coated tablet (Viagra®, available from Pfizer Inc.) for the treatment of erectile dysfunction. However, the reported bioavailability of this formulation is only 40%.

Sildenafil citrate is also commercially available in formulations for the treatment of pulmonary arterial hypertension. One such formulation is a film coated tablet (Revatio®, available from Pfizer Inc.).

"Sublingual" means "under the tongue" and refers to administration of a substance via the mouth in such a way that the substance is rapidly absorbed via the blood vessels under the tongue. A sublingual formulation is desirable because it bypasses hepatic first pass metabolic processes which provide better bioavailability, rapid onset of action, and higher patient compliance. Dysphagia (difficulty in swallowing) is common among in all ages of people and more common in geriatric patients. In terms of permeability, the sublingual area of oral cavity is more permeable than buccal area. Sublingual drug administration is applied in field of cardiovascular drugs, analgesics, steroids, enzymes and barbiturates.

U.S. Pat. No. 6,548,490 is directed to methods for treating erectile dysfunction including sublingually administering a composition that can include sildenafil. This method requires that the composition be in the form of a tablet, cream, ointment or paste. U.S. Pat. No. 8,133,903 discloses a method that includes administering up to 1.5 mg/kg/day of a PDE5 inhibitor, such as sildenafil, for not less than 45 days. This patent, however, also fails to disclose a fast acting oral spray formulation.

US Patent Application Publication No. 20130059854 discloses a method for mitigating erectile dysfunction by administering a composition orally that can include sildenafil. This formulation requires the use of sucrose fatty acid esters. U.S. Pat. No. 7,758,886 is directed to an aerosol composition including a poorly water-soluble active agent, such as sildenafil. This patent teaches that tyloxapol, polysorbates, vitamin E TPGS, or macrogol-hydroxystearates, and a phospholipid component, are required for administration. U.S. Pat. No. 6,585,958 discloses an aerosol formulation that may contain sildenafil. This formulation, however, requires a pressure-liquefied propellant mixture that includes dinitrogen monoxide and other components. In addition, US Patent Application Publication No. 20130143894 discloses a sildenafil oral spray formulation wherein the pH is from about 1.5 to less than 3.0. This application, however, teaches the use of a polar solvent such as propylene glycol and ethyl alcohol.

While there are various sildenafil formulations currently available, there is still a need in the art for a quick-onset sublingual spray formulation containing sildenafil.

SUMMARY OF THE INVENTION

In one aspect, the present invention is directed to sublingual spray formulation comprising from about 5% w/w to about 35% w/w sildenafil or a salt thereof, from about 0.1% w/w to about 60% w/w of at least one pharmacologically acceptable polar solvent selected from the group consisting of purified water, ethanol, and polyethylene glycol 400, an excipient selected from the group consisting of from about 0.1% w/w to about 50% w/w glycerol, from about 0.1% w/w to about 50% w/w propylene glycol and a combination thereof, and from about 0.1% w/w to about 60% w/w of at least one acid selected from the group consisting of an inorganic acid and an organic acid.

In another aspect, the present invention is directed to a propellant free sublingual spray formulation comprising from about 5% w/w to about 20% w/w sildenafil or a salt thereof, from about 35% w/w to about 55% w/w ethanol, from about 1% w/w to about 30% w/w water, an excipient selected from the group consisting of from about 5% w/w to about 30% w/w glycerol, from about 5% to about 30% propylene glycol, from about 5% to about 30% polyethylene glycol 400 and from about 0.1% w/w to about 60% w/w diluted hydrochloric acid.

In another aspect, the present invention is directed to a propellant free sublingual spray formulation comprising about 8% w/w sildenafil or a salt thereof, about 40% w/w ethanol, about 10% w/w glycerol, about 26% w/w water, about 12% w/w diluted hydrochloric acid; and a permeation enhancer comprising 0.5% w/w menthol and 2% w/w caprylic acid.

In another aspect, the present invention is directed to methods for treating male sexual dysfunction comprising administering the formulations of the present invention to a patient.

In a further aspect, the present invention is directed to methods for treating pulmonary arterial hypertension comprising administering the formulations of the present invention to a patient.

DETAILED DESCRIPTION

Applicant unexpectedly discovered sublingual sildenafil formulations that have improved bioavailability, a more rapid absorption, and improved storage stability.

In one embodiment, the present invention is directed to sublingual spray formulation comprising from about 5% w/w to about 35% w/w sildenafil or a salt thereof, from about 0.1% w/w to about 60% w/w of at least one pharmacologically acceptable polar solvent selected from the group consisting of purified water, ethanol, and polyethylene glycol 400, an excipient selected from the group consisting of from about 0.1% w/w to about 50 w/w glycerol and from about 0.1% to about 50% propylene glycol, and from about 0.1% w/w to about 60% w/w of at least one acid selected from the group consisting of an inorganic acid and an organic acid.

In a preferred embodiment, the sublingual spray formulation comprises from about 5% w/w to about 20% w/w sildenafil or a salt thereof. In a more preferred embodiment, the sublingual spray formulation comprises about 8% w/w, about 16% w/w, or about 20% w/w sildenafil or a salt thereof.

In a one embodiment, the acid is an inorganic acid or an organic acid.

In another embodiment, the acid is an organic acid selected from the group consisting of malic acid, tartaric acid, citric acid, lactic acid, formic acid, acetic acid, succinic acids, and a combination thereof.

In another embodiment, the acid is an inorganic acid selected from the group consisting of hydrochloric acid, hydrobromic acid, hydrofluoric acid, phosphoric acid, sulfuric acid, nitric acid, sulfonic acid, and a combination thereof.

In a preferred embodiment, the acid is an inorganic acid. In a more preferred embodiment, the inorganic acid is hydrochloric acid that is diluted or concentrated.

In one embodiment, the hydrochloric acid is diluted to from about 1N to about 11N. In a preferred embodiment, the hydrochloric acid is diluted to from about 1.5N to about 6N. In a more preferred embodiment, the hydrochloric acid is diluted to about 1.5N or about 3N.

In another embodiment, the formulations contain from about 0.1% w/w to about 50% water. In a preferred embodiment, the formulations contain from about 1% w/w to about 30% w/w water. In another preferred embodiment, the formulations contain from about 1% w/w to about 15% w/w water. In another preferred embodiment, the formulations contain from about 1% w/w to about 10% w/w water. In another preferred embodiment, the formulations contain about 11% w/w, about 14% w/w, about 26% w/w or about 31% w/w water.

In yet another embodiment, the formulations contain from about 10% w/w to about 60% w/w ethanol. In a preferred embodiment, the formulations contain from about 20% w/w to about 50% w/w ethanol. In another preferred embodiment, the formulations contain from about 35% w/w to about 55% w/w ethanol. In another preferred embodiment, the formulations contain about 37% w/w, about 38% w/w, about 39% w/w, about 40% w/w, about 45% w/w or about 50% w/w ethanol.

In an embodiment, the formulations contain from about 5% w/w to about 50% w/w glycerol. In a preferred embodiment, the formulations contain from about 10% w/w to about 40% w/w glycerol. In a more preferred embodiment, the formulations contain from about 5% w/w to about 30% w/w glycerol. In another preferred embodiment, the formulations contain about 5% w/w, about 10% w/w, about 12.5% w/w, about 15% w/w, about 20% w/w, about 25% w/w, about 27% w/w, about 28% w/w, about 29% w/w, about 30% w/w, about 32% w/w and about 35% w/w glycerol.

In a further embodiment, the formulations contain from about 0.1% w/w to about 50% w/w propylene glycol. In a more preferred embodiment, the formulations contain from about 0.1% w/w to about 40% w/w propylene glycol. In another preferred embodiment, the formulations contain from about 5% w/w to about 30% w/w propylene glycol. In another embodiment, the formulation contain about 5% w/w, about 10% w/w, about 12.5% w/w, about 15% w/w about 20% w/w, about 25% w/w, about 27% w/w, about 28% w/w, about 29% w/w, about 30% w/w, about 32% w/w and about 35% w/w propylene glycol.

In another embodiment, the formulations contain from about 0.1% w/w to about 50% w/w polyethylene glycol 400. In a more preferred embodiment, the formulations contain from about 10% w/w to about 40% w/w polyethylene glycol 400.

Preferably, the formulations of the present invention are propellant free.

In another embodiment, the formulations of the present invention contain sildenafil in the form of a base or an acid.

In another embodiment, the formulations contain a pharmaceutically acceptable salt of sildenafil. In a preferred embodiment, the formulations contain a salt selected from the group consisting of citrate, hydrochloride, halide, sulfate, phosphate, acetate, maleate, succinate, ascorbate, carbonate, mesylate and lactate. One of skill in the art could use other pharmaceutically acceptable sildenafil salts in the formulations of the present invention.

In a further embodiment, the formulation contains an antioxidant and/or stabilizer, a permeation enhancer, a sweetener, a sweetness enhancer, a pH modifier, a flavoring agent, a preservative, or a combination thereof.

In a preferred embodiment, the formulations may contain an antioxidant and/or stabilizer. In a more preferred embodiment, the antioxidant and/or stabilizer is selected from the group consisting of ascorbyl palmitate, ascorbic acid, dl-alpha tocopherol, butylated hydroxytoluene, butylated hydroxyanisole, cysteine HCl, citric acid, ethylenediamine tetra acetic acid (EDTA), methionine, citric acid, sodium citrate, sodium ascorbate, sodium thiosulfate, sodium metabisulfite, sodium bisulfite, propyl gallate, glutathione and thioglycerol. Other appropriate antioxidants known by those of skill in the art could also be added to formulations of the present invention. In a preferred embodiment, the formulations contain from about 0.001% w/w to about 1% w/w of the antioxidant. In a more preferred embodiment, the formulations may contain from about 0.005% w/w to about 0.05% w/w of the antioxidant.

In another embodiment, the formulation contains a permeation enhancer. In a preferred embodiment, the permeation enhancer is selected from the group consisting of menthol, limonene, carvone, methyl chitosan, polysorbates including Tween® 80 (polysorbate 80; Tween is a registered trademark of Uniqema Americas, LLC), sodium lauryl sulfate, glyceryl oleate, caproic acid, enanthic acid, caprylic acid, pelargonic acid, capric acid, undecylenic acid, lauric acid, myristic acid, palmitic acid, oleic acid, stearic acid, linolenic acid, arachidonic acid, benzethonium chloride, benzethonium bromide, benzalkonium chloride ("BKC"), cetylpyridium chloride, edetate disodium dihydrate, sodium desoxycholate, sodium deoxyglycolate, sodium glycocholate, sodium caprate, sodium taurocholate, sodium hydroxybenzoyl amino caprylate, dodecyl dimethyl aminopropionate, L-lysine, glycerol oleate, glyceryl monostearate, citric acid, peppermint oil and a combination thereof. In a preferred embodiment the permeation enhancer is selected from the group consisting of menthol, a medium chain glyceride or a medium chain fatty acid such as caproic acid, enanthic acid, caprylic acid, pelargonic acid, capric acid, undecylenic acid or lauric acid, BKC and a combination thereof. In a more preferred embodiment the medium chain fatty acid is caprylic acid or capric acid, preferably caprylic acid.

In a preferred embodiment the formulations contain from about 0.5% to about 20% w/w of a permeation enhancer.

In another preferred embodiment, the formulations contain from about 0.1% w/w to about 20% w/w of caprylic acid.

In another preferred embodiment, the formulations contain from about 0.1% w/w to about 10% w/w of caprylic acid.

In another preferred embodiment, the formulations contain from about 0.1% w/w to about 5% w/w of caprylic acid.

In a preferred embodiment, the permeation enhancer is selected from the group consisting of menthol in an amount from about 0.001% to about 20.0% w/w, caprylic acid in an amount from about 0.1% to 10% w/w, BKC in an amount from about 0.001% to 10% w/w and a combination thereof.

In another preferred embodiment, the permeation enhancer is selected from the group consisting of about 0.01% to 1% w/w menthol, about 0.1% to 10% w/w caprylic acid, about 0.001 to 0.2% w/w BKC, about 0.01 to 1% w/w cetylpyridinium chloride and a combination thereof.

In another preferred embodiment, the permeation enhancer is 0.5% w/w menthol and 2% w/w caprylic acid.

In another preferred embodiment, the permeation enhancer is 0.5% w/w menthol 0.01% w/w BKC and 2% w/w caprylic acid.

In another preferred embodiment, the permeation enhancer is 0.5% w/w menthol 0.1% w/w cetylpyridinium chloride and 2% w/w caprylic acid.

In a preferred embodiment, the formulations contain a sweetener. In a more preferred embodiment, the sweetener is selected from the group consisting of sucralose, aspartame, saccharin, dextrose, mannitol, glycerin, mannitol and xylitol.

In a further embodiment, the formulation may contain a sweetness enhancer, an ammonium salt form of crude and refined Glycyrrhizic Acid, for example, Magnasweet® product (available from Mafco Worldwide Corporation, Magnasweet is a registered trademark of Mafco Worldwide Corporation). Magnasweet® products use the ammonium salt forms of crude and refined Glycyrrhizic Acid. Glycyrrhizic Acid is also available as a pure derivative in the sodium and potassium salt forms.

In another embodiment, the formulations contain a pH modifier. In a preferred embodiment, the pH modifier adjusts the pH of the formulation to from about 2 and about 6. In a more preferred embodiment, the pH modifier adjusts the pH of the formulation to from about 2 and about 5. In a most preferred embodiment, the pH modifier adjusts the pH of the formulation to about 4.5±0.2. In another most preferred embodiment, the pH is 3±0.2 or greater.

In another embodiment, the formulations contain a flavoring agent. In a preferred embodiment, the formulations contain a flavoring agent selected from the group consisting of peppermint oil, menthol, spearmint oil, citrus oil, cinnamon oil, strawberry flavor, cherry flavor, raspberry flavor, orange oil, and a combination thereof. Other appropriate flavoring agents known by those of skill in art could also be added to formulations of the present invention. In a preferred embodiment, the formulations contain from about 0.001% w/w to about 1% w/w of the flavoring agent. In a more preferred embodiment, the formulations contain from about 0.005% w/w to about 0.5% w/w of the flavoring agent.

In yet another embodiment, the formulations may contain a preservative. In a preferred embodiment, the preservative is selected from the group consisting of butyl paraben, methyl paraben, ethyl paraben, propyl paraben, sodium benzoate, benzyl alcohol, sorbic acid and benzoic acid. In a preferred embodiment, the formulations contain from about 0.001% w/w to about 1% w/w of the preservative. In a more preferred embodiment, the formulations contain from about 0.005% w/w to about 0.05% w/w of the preservative.

In a further embodiment, the present invention is directed to propellant free sublingual spray formulations comprising from about 5% w/w to about 20% w/w sildenafil or a salt thereof, from about 35% w/w to about 55% w/w ethanol, from about 1% w/w to about 30% w/w water, an excipient selected from the group consisting of about 5% w/w to about 35% w/w glycerol and from about 5% to about 30% propylene glycol, and from about 0.1% w/w to about 60% w/w diluted hydrochloric acid and optionally a permeation enhancer selected from menthol, caprylic acid, benzalkonium chloride, cetylpyridinium chloride and a combination thereof.

In another aspect, the present invention is directed to a propellant free sublingual spray formulation comprising about 8% w/w sildenafil or a salt thereof, about 40% w/w ethanol, about 10% w/w glycerol, about 26% w/w water, about 12% w/w diluted hydrochloric acid, and a permeation enhancer comprising 0.5% w/w menthol and 2% w/w caprylic acid.

In another aspect, the present invention is directed to a propellant free sublingual spray formulation comprising about 8% w/w sildenafil or a salt thereof, about 50% w/w ethanol, about 15% w/w glycerol, about 12% w/w water, about 12% w/w diluted hydrochloric acid, and a permeation enhancer comprising 0.5% w/w menthol, 0.1% cetylpyridinium chloride and 2% w/w caprylic acid.

In another aspect, the present invention is directed to a propellant free sublingual spray formulation comprising about 8% w/w sildenafil or a salt thereof, about 50% w/w ethanol, about 15% w/w propylene glycol, about 12% w/w water, about 12% w/w diluted hydrochloric acid, and a permeation enhancer comprising 0.5% w/w menthol, 0.1% cetylpyridinium chloride and 2% w/w caprylic acid.

In an alternative embodiment, the present invention is directed to methods for treating sexual dysfunction in men comprising administering formulations of the present invention to a patient in need thereof.

In a preferred embodiment, the formulations of the present invention are delivered via a spray pump to treat sexual dysfunction. In a more preferred embodiment, the spray pumps deliver from about 50 to about 400 µL to the patient. In a most preferred embodiment, the formulations are delivered under the patient's tongue.

In another embodiment, the present invention is directed to methods for treating pulmonary arterial hypertension in a human comprising administering the formulation of claim 1 to a patient in need thereof.

In a preferred embodiment, the formulations of the present invention are delivered via a spray pump to treat arterial hypertension. In a more preferred embodiment, the spray pumps deliver from about 50 to about 400 µL to the patient. In a most preferred embodiment, the formulations are delivered under the patient's tongue.

In another embodiment, the invention is directed to methods for treating sexual dysfunction in men comprising administering formulations of the present invention to a patient in need of such treatment.

In yet another embodiment, the invention is directed to methods for treating pulmonary arterial hypertension in humans comprising administering formulations of the present invention to a patient in need of such treatment.

In a preferred embodiment, the formulations of the present invention do not discolor when stored at 40° C. or 55° C.

In yet another embodiment, the formulations of the present invention are capable of producing a droplet size distribution wherein the mean Dv(10) is from about 18 to about 25 microns during administration.

In a further embodiment, the formulations of the present invention are capable of producing a droplet size distribution wherein the mean Dv(50) is from about 50 to about 70 microns during administration.

In yet another embodiment, the formulations of the present invention are capable of producing a droplet size distribution wherein the mean Dv(90) is from about 250 to about 500 microns during administration. Preferably, the formulations of the present invention are capable of producing a droplet size distribution wherein the mean Dv(90) is from about 400 to about 500 microns during administration.

In yet another embodiment, the formulations of the present invention are capable of producing a spray span ((Dv90–Dv10)/Dv50) of from about 4 to about 7. Preferably, the formulations of the present invention are capable of producing a spray span ((Dv90–Dv10)/Dv50) of from about 5 to about 7.

As used herein, "sildenafil" refers to the base or a pharmaceutically acceptable salt, ester, derivative, or prodrug thereof.

As used herein, "propellant free" refers to a formulation that is not administered using compressed gas.

As used herein, "male sexual dysfunction" refers to erectile dysfunction or impotence. Erectile dysfunction and impotence are characterized by the inability to develop or maintain an erection of the penis during sexual activities.

As used herein, "pulmonary arterial hypertension" refers to the condition of having abnormally high blood pressure in the lungs.

As used herein, all numerical values relating to amounts, weights, and the like, that are defined as "about" each particular value is plus or minus 10%. For example, the phrase "about 10% w/w" is to be understood as "9% w/w to 11% w/w." Therefore, amounts within 10% of the claimed value are encompassed by the scope of the claims.

As used herein "% w/w" and "percent w/w" refer to the percent weight of the total formulation.

As used herein the term "effective amount" refers to the amount necessary to treat a patient in need thereof.

As used herein the term "patient" refers, but is not limited to, a person that is being treated for male sexual dysfunction or pulmonary arterial hypertension.

As used herein the term "pharmaceutically acceptable" refers to ingredients that are not biologically or otherwise undesirable in a sublingual dosage form.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to use the formulations of the invention. They are not intended to be limiting in any way.

EXAMPLES

Example 1

Preparation of a Sildenafil Sublingual Formulation

In order to prepare a sildenafil sublingual formulation, the components as indicated in "Table 1. The Components of Formulation 1" below were weighed. The components were mixed until a clear solution was formed.

Sildenafil base U.S.P. (available from Pol Pharma) was used as the source of sildenafil in the formulations that follow. Ethanol, 200 Proof, denatured, U.S.P., (available from Spectrum) was used as the source of alcohol. Strawberry flavor, Nat&Art 915.0543 U, (available from FONA) was used as the source of flavoring. L-menthol, crystal, U.S.P., was also used as the source of flavoring. Sucralose, N.F., (available from Spectrum) was used as the source of sweetener. Glycerol, U.S.P., 99.0-100.5%, (available from EMD Milipore) was used as solvent and nucleation inhibitor. Water, U.S.P., purified, (available from RICCA) was used as the source of solvent. 3N HCL, U.S.P. (Prepared from J.T baker 6N) was used as the source of acid.

TABLE 1

The Components of Formulation 1

| | % w/w |
|---|---|
| Sildenafil base | 15.8 |
| Ethanol | 40 |
| Flavoring agent | 0.15 |
| L-menthol | 0.05 |
| Sucralose | 0.8 |
| Glycerol | 28 |
| Water | 3.5 |
| 3N HCL | 11.8 |
| pH adjusted to 4.5 with 3.0N NaOH | 100 |

Example 2

Preparation of Additional Sildenafil Sublingual Formulations

In order to prepare a sildenafil sublingual formulation, the components as indicated in "Table 2. The Components of Formulations 2A to 2K" below were weighed. The components were mixed until a clear solution was formed.

Sildenafil base U.S.P. (available from Pol Pharma) was used as the source of sildenafil in the formulations that follow. Ethanol, 200 Proof, denatured, U.S.P., (available from Spectrum) was used as the source of alcohol. Strawberry flavor, Nat&Art 915.0543 U, (available from FONA) was used as the source of flavoring. L-menthol, crystal, U.S.P., was also used as the source of flavoring. Sucralose, N.F., (available from Spectrum) was used as the source of sweetener. Glycerol, U.S.P., 99.0-100.5%, (available from EMD Milipore) was used as the source of solvent. Water, U.S.P., purified, (available from RICCA) was used as the source of another solvent. 3N HCL, U.S.P. (available from J.T. Baker) was used as the source of acid.

TABLE 2

The Components of Formulation 2A to 2K

| % w/w | 2A | 2B | 2C | 2D | 2E | 2F | 2G | 2H | 2I | 2J | 2K |
|---|---|---|---|---|---|---|---|---|---|---|---|
| Sildenafil base | 16 | 16 | 16 | 16 | 16 | 16 | 16 | 16 | 16 | 16 | 15.8 |
| Ethanol | 40 | 39 | 37.5 | 37.5 | 36.8 | 39 | 39 | 40 | 40 | 38 | 40 |
| Flavoring | — | — | — | — | — | 0.15 | 0.15 | — | — | 0.15 | 0.15 |
| L-menthol | — | — | — | — | — | — | — | — | — | — | 0.5 |
| Sucralose | — | — | — | — | — | 0.8 | 0.8 | — | — | 0.8 | 0.8 |
| Ammonium salt form of crude and refined Glycyrrhizic Acid | — | — | — | — | — | 0.05 | 0.05 | — | — | 0.05 | — |
| Polyvinylpyrrolidone | — | — | — | — | — | — | 0.5 | — | 1 | — | — |
| Glycerol | 25 | 30 | 30 | 32.2 | 34.7 | 28.7 | 28.2 | 27.5 | 27 | 30 | 28 |
| Water | 7.5 | 5 | 5 | 2.8 | 1 | 3.8 | 3.8 | 4.5 | 4.5 | 3.5 | 3.47 |
| 3N HCL (Diluted from 6N HCL) | 11.5 | 11.5 | 11.5 | 11.5 | 11.5 | 11.5 | 11.5 | 11.5 | 11.5 | 11.5 | 11.75 |

Example 3

Preparation of Additional Sildenafil Sublingual Formulations

TABLE 3

The Components of Formulations 3A and 3B

| % w/w | 3A | 3B |
|---|---|---|
| Sildenafil base | 20 | 20 |
| Ethanol | 44.5 | 40 |
| Glycerol | 20 | 25 |
| Water | 1 | 1 |
| 3N HCL | 14.5 | 14 |

Example 4

Preparation of Additional Sildenafil Sublingual Formulations

Sildenafil base U.S.P. (available from Pol Pharma) was used as the source of sildenafil in the formulations that follow. Strawberry flavor, Nat&Art 915.0543 U, (available from FONA) was used as the source of flavoring. L-menthol, crystal, U.S.P., was also used as the source of flavoring. Sucralose, N.F., (available from Spectrum) was used as the source of sweetener. Glycerol, U.S.P., 99.0-100.5%, (available from EMD Milipore) was used as the source of solvent. Water, U.S.P., purified, (available from RICCA) was used as the source of another solvent. 1.5 N HCl or 3N HCl, U.S.P. (available from J.T. Baker) was used as the source of acid.

Example 5

In order to determine the stability of formulations of the present invention, the formulations were subjected to standard stability testing. The results of one of these tests is below in "Table 4. Stability of Formulations 3A and 3B".

TABLE 4

The Components of Formulations 4A through 4L

| % w/w | 4A | 4B | 4C | 4D | 4E | 4F | 4G | 4H | 4I | 4J | 4K | 4L |
|---|---|---|---|---|---|---|---|---|---|---|---|---|
| Sildenafil base | 16.56 | 16.56 | 16.56 | 8.28 | 8.28 | 8.28 | 8.28 | 16.56 | 8.28 | 8.28 | 8.28 | 8.28 |
| Ethanol | 40 | 40 | 22.5 | 40 | 40 | 40 | 40 | 40 | 50 | 50 | 50 | 50 |
| Malic Acid | — | — | 30 | — | — | — | — | — | — | — | — | — |
| Flavoring | 0.15 | 0.15 | — | 0.15 | 0.15 | 0.15 | 0.15 | 0.15 | 0.15 | 0.15 | 0.15 | 0.15 |
| L-menthol | 0.05 | 0.05 | — | 0.5 | 0.5 | 0.5 | 0.5 | 0.5 | 0.5 | 0.5 | 0.5 | 0.5 |
| Cetylpyridinium chloride | — | — | — | — | — | — | — | — | 0.1 | 0.1 | 0.1 | 0.1 |
| Sucralose | 0.8 | 0.8 | — | 0.8 | 0.8 | 0.8 | 0.8 | 0.8 | 0.8 | 0.8 | 0.8 | 0.8 |
| Propylene glycol | 28 | — | — | — | 5 | — | 10 | — | — | — | 15 | 12.5 |
| Glycerol | — | 28 | — | 5 | — | 10 | — | 25 | 15 | 12.5 | — | — |
| Water | 2.11 | 2.11 | 30.94 | 30.94 | 30.94 | 25.94 | 25.94 | 2.66 | 11.42 | 13.92 | 11.42 | 13.92 |
| Caprylic Acid | — | — | 2 | 2 | 2 | 2 | 2 | 2 | 2 | 2 | 2 | 2 |
| 1.5N HCl | — | — | — | — | — | 12.33 | 12.33 | — | 11.75 | 11.75 | 11.75 | 11.75 |
| 3N HCl | 12.33 | 12.33 | — | 12.33 | 12.33 | — | — | 12.33 | — | — | — | — |
| pH | 4.5 ± 0.1 | 4.5 ± 0.1 | 2.45 | 4.5 ± 0.1 | 4.5 ± 0.1 | 4.5 ± 0.1 | 4.5 ± 0.1 | 4.5 ± 0.1 | 3.0 ± 0.2 | 3.0 ± 0.2 | 3.0 ± 0.2 | 3.0 ± 0.2 |

TABLE 5

Stability of Formulations 3A and 3B

| Formulation # | Label Claim (mg/mL) | | T0 Conc (mg/mL) | T0 % of Initial Conc | 1 Week Conc (mg/mL) | 1 Week % of Initial Conc | 2 Weeks Conc (mg/mL) | 2 Weeks % of Initial Conc |
|---|---|---|---|---|---|---|---|---|
| 3A | 200.4 | 5° C. | 199.18 | 100.00% | 197.56 | 99.20% | | |
| | | 25° C. | | | 199.04 | 99.90% | | |
| | | 40° C. | | | 199.13 | 100.00% | 199.72 | 100.30% |
| | | 55° C. | | | | | 199.85 | 100.30% |
| 3B | 202.8 | 5° C. | 202.86 | 100.00% | 201.91 | 99.50% | | |
| | | 25° C. | | | 203.36 | 100.20% | | |
| | | 40° C. | | | 202.69 | 99.90% | 205.28 | 101.20% |
| | | 55° C. | | | | | 202.72 | 99.90% |

| Formulation # | Label Claim (mg/mL) | | 4 Weeks Conc (mg/mL) | 4 Weeks % of Initial Conc | 6 Weeks Conc (mg/mL) | 6 Weeks % of Initial Conc | 8 Week Conc (mg/mL) | 8 Week % of Initial Conc |
|---|---|---|---|---|---|---|---|---|
| 3A | 200.4 | 5° C. | | | | | | |
| | | 25° C. | | | | | | |
| | | 40° C. | 201.02 | 100.90% | 200.13 | 100.50% | 200.79 | 100.80% |
| | | 55° C. | 201.76 | 101.30% | 203.18 | 102.00% | 201.91 | 101.40% |
| 3B | 202.8 | 5° C. | | | | | | |
| | | 25° C. | | | | | | |
| | | 40° C. | 204.11 | 100.60% | 204.86 | 101.00% | 200.89 | 99.00% |
| | | 55° C. | 201.55 | 99.40% | 204.09 | 100.60% | 204.93 | 101.00% |

As can be seen in Table 5, the formulations maintained high concentrations of sildenafil as determined by chemical analysis.

In order to further determine the stability of Formulations 3A and 3B, the formulations were subjected to standard stability testing. The results are below in "Table 6. Stability of Formulations 3A and 3B at 40 Degrees Celsius" and "Table 7. Stability of Formulations 3A and 3B at 55 Degrees Celsius."

TABLE 6

Stability of Formulations 3A and 3B at 40 Degrees Celsius

| FORMULATION # 3A, 40° C./75% RH | | | Drug | | | | | | |
|---|---|---|---|---|---|---|---|---|---|
| | RRT | Specification | Substance | t = 0 | 1 week | 2 weeks | 4 weeks | 6 weeks | 8 weeks |
| Physical appearance | | | clear, colorless | clear, colorless | clear, colorless | clear, colorless | clear, colorless | clear, colorless | clear, colorless |
| Assay (% of initial Conc) | | 95.0-105.0% | 100.70% | 99.60% | 99.40% | 99.70% | 100.90% | 100.50% | 100.00% |
| Impurity A | 1.16 | <0.15% | BQL | BQL | BQL | BQL | BQL | BQL | BQL |
| Impurity B | 0.64 | <0.15% | ND | BQL | ND | BQL | ND | BQL | BQL |
| Impurity C | 0.57 | <0.15% | BQL | ND | ND | ND | ND | BQL | ND |
| Impurity D | 0.25 | <0.15% | BQL | BQL | BQL | BQL | BQL | BQL | BQL |
| Unknown Impurity RRT 0.24 | 0.24 | <0.10% | ND | ND | ND | ND | ND | ND | ND |
| Unknown Impurity RRT 0.61 | 0.61 | <0.10% | ND | BQL | BQL | BQL | BQL | BQL | BQL |
| Total Impurities: | | <0.50% | 0.00% | 0.00% | 0.00% | 0.00% | 0.00% | 0.00% | 0.00% |
| FORMULATION # 3B, 40° C./75% RH | | | Drug | | | | | | |
| | RRT | Specification | Substance | t = 0 | 1 week | 2 weeks | 4 weeks | 6 weeks | 8 weeks |
| Physical appearance | | | clear, colorless | clear, colorless | clear, colorless | clear, colorless | clear, colorless | clear, colorless | clear, colorless |
| Assay (% of initial Conc) | | 95.0-105.0% | 100.70% | 101.40% | 99.90% | 101.20% | 101.30% | 101.00% | 99.10% |
| Impurity A | 1.16 | <0.15% | BQL | BQL | BQL | BQL | BQL | BQL | BQL |
| Impurity B | 0.64 | <0.15% | ND | BQL | ND | BQL | BQL | BQL | BQL |

TABLE 6-continued

Stability of Formulations 3A and 3B at 40 Degrees Celsius

| | RRT | Specification | t=0 | | | | | | |
|---|---|---|---|---|---|---|---|---|---|
| Impurity C | 0.57 | <0.15% | BQL | ND | ND | ND | ND | ND | ND |
| Impurity D | 0.25 | <0.15% | BQL | BQL | BQL | BQL | BQL | BQL | BQL |
| Unknown Impurity RRT 0.24 | 0.24 | <0.10% | ND | ND | ND | ND | ND | ND | ND |
| Unknown Impurity RRT 0.61 | 0.61 | <0.10% | ND | BQL | BQL | BQL | BQL | BQL | BQL |
| Total Impurities: | | <0.50% | 0.00% | 0.00% | 0.00% | 0.00% | 0.00% | 0.00% | 0.00% |

TABLE 7

Stability of Formulations 3A and 3B at 55 Degrees Celsius

FORMULATION # 3A, 55° C.

| | RRT | Specification | Drug Substance t = 0 | 2 weeks | 4 weeks | 6 weeks | 8 weeks |
|---|---|---|---|---|---|---|---|
| Physical appearance | | | clear, colorless | clear, colorless | clear, colorless | clear, colorless | clear, colorless | clear, colorless |
| Assay (% of initial Conc) | | 95.0-105.0% | 100.70% | 99.60% | 99.70% | 100.60% | 102.00% | 100.80% |
| Impurity A | 1.16 | <0.15% | BQL | BQL | BQL | BQL | BQL | BQL |
| Impurity B | 0.64 | <0.15% | ND | BQL | BQL | BQL | BQL | BQL |
| Impurity C | 0.57 | <0.15% | BQL | ND | ND | BQL | ND | BQL |
| Impurity D | 0.25 | <0.15% | BQL | BQL | BQL | BQL | BQL | BQL |
| Unknown Impurity RRT 0.24 | 0.24 | <0.10% | ND | ND | ND | ND | ND | ND |
| Unknown Impurity RRT 0.61 | 0.61 | <0.10% | ND | BQL | BQL | BQL | BQL | BQL |
| Total Impurities: | | <0.50% | 0.00% | 0.00% | 0.00% | 0.00% | 0.00% | 0.00% |

FORMULATION # 3B, 55° C.

| | RRT | Specification | Drug Substance t = 0 | 2 weeks | 4 weeks | 6 weeks | 8 weeks |
|---|---|---|---|---|---|---|---|
| Physical appearance | | | clear, colorless | clear, colorless | clear, colorless | clear, colorless | clear, colorless | clear, colorless |
| Assay (% of initial Conc) | | 95.0-105.0% | 100.70% | 101.40% | 100.00% | 99.40% | 100.60% | 101.00% |
| Impurity A | 1.16 | <0.15% | BQL | BQL | BQL | BQL | BQL | BQL |
| Impurity B | 0.64 | <0.15% | ND | BQL | BQL | BQL | BQL | BQL |
| Impurity C | 0.57 | <0.15% | BQL | ND | ND | BQL | BQL | BQL |
| Impurity D | 0.25 | <0.15% | BQL | BQL | BQL | BQL | BQL | BQL |
| Unknown Impurity RRT 0.24 | 0.24 | <0.10% | ND | ND | ND | ND | ND | ND |
| Unknown Impurity RRT 0.61 | 0.61 | <0.10% | ND | BQL | BQL | BQL | BQL | BQL |
| Total Impurities: | | <0.50% | 0.00% | 0.00% | 0.00% | 0.00% | 0.00% | 0.00% |

As can be seen in Tables 6 and 7, the formulations were observed to be clear and colorless. The formulations also had low levels of impurities as determined by chemical analysis. "ND" means that the impurity was not detected and "BQL" means that the impurity was below a quantifiable limit. Relative retention time "RRT" is given for each impurity.

In order to further determine the stability of Formulations 3A and 3B, the formulations were subjected to standard freeze/thaw stability testing. The results are below in "Table 8. Stability of Formulations 3A and 3B to Freeze/Thaw Testing."

TABLE 8

Stability of Formulations 3A and 3B to Freeze/Thaw Testing

| Formulation # 3A | Drug Substance | t = 0 | Cycle 1, −20° C. | Cycle 1, 25° C. | Cycle 2, −20° C. | Cycle 2, 25° C. | Cycle 3, −20° C. | Cycle 3, 25° C. |
|---|---|---|---|---|---|---|---|---|
| Date Observed: Physical appearance Color | clear colorless | Nov. 26, 2014 clear colorless | Dec. 1, 2014 clear colorless | Dec. 3, 2014 clear colorless | Dec. 5, 2014 clear colorless | Dec. 8, 2014 clear colorless | Dec. 10, 2014 clear colorless | Dec. 12, 2014 clear colorless |
| Formulation # 3B | Drug Substance | t = 0 | Cycle 1, −20° C. | Cycle 1, 25° C. | Cycle 2, −20° C. | Cycle 2, 25° C. | Cycle 3, −20° C. | Cycle 3, 25° C. |
| Date Observed: Physical appearance Color | clear colorless | Nov. 26, 2014 clear colorless | Dec. 1, 2014 clear colorless | Dec. 3, 2014 clear colorless | Dec. 5, 2014 clear colorless | Dec. 8, 2014 clear colorless | Dec. 10, 2014 clear colorless | Dec. 12, 2014 clear colorless |

As seen in Table 8, no crystals developed and the formulations remained stable despite the harsh conditions. Further, Applicant determined that total and individual impurities were within acceptable limits.

In addition, Formulations 2A to 2I were subjected to stability testing. A summary of these results is below in "Table 9. Stability of Formulations 2A to 2I to 22 Degrees Celsius and Freeze/Thaw Studies."

TABLE 9

Stability of Formulations 2A to 2I to 22 Degrees Celsius and Freeze/Thaw Studies

| Formulation | Days Accomplished | Physical Observation | | | Cycle 1 Freeze-Thaw Cycle | | Cycle 2 Freeze-Thaw Cycle | | Cycle 3 Freeze-Thaw Cycle | |
|---|---|---|---|---|---|---|---|---|---|---|
| | | Room Temp (22° C.) | 5° C. | −20° C. | Freeze (−20° C.) | Thaw (22° C.) | Freeze (−20° C.) | Thaw (22° C.) | Freeze (−20° C.) | Thaw (22° C.) |
| 2A | 2 Months | Clear | Clear | Crystal growth (After 10 days) | clear | clear | clear | clear | clear | clear |
| 2B | 2 Months | Clear | Clear | Crystal growth (After 10 days) | clear | clear | clear | clear | clear | clear |
| 2C | 2 Months | Clear | Clear | Crystal growth (After 7 days) | clear | clear | clear | clear | clear | clear |
| 2D | 2 Months | Clear | Clear | Crystal growth (After 7 days) | clear | clear | clear | clear | clear | clear |
| 2E | 2 Months | Clear | Clear | Crystal growth (After 14 days) | clear | clear | clear | clear | clear | clear |
| 2F | 2 Months | Clear | Clear | Crystal growth (After 14 days) | clear | clear | clear | clear | clear | clear |
| 2G | 2 Months | Clear | Clear | Crystal growth (After 14 days) | clear | clear | clear | clear | clear | clear |
| 2H | 2 Months | Clear | Clear | Crystal growth (After 14 days) | clear | clear | clear | clear | clear | clear |
| 2I | 2 Months | Clear | Clear | Crystal growth (After 16 days) | clear | clear | clear | clear | clear | clear |

As seen in Table 9, no crystals developed and the formulations remained stable despite the harsh conditions.

Further, Formulation 1 was subjected to stability testing. A summary of these results is below in "Table 10. Stability of Formulation 1 at 55° C.," and "Table 11. Stability of Formulation 1 to Freeze/Thaw Testing."

TABLE 10

Stability of Formulation 1 at 55° C.

| Formulation # 1 | RRT | Specifications | T0 | 2 Week | 3 Week | 4 Week | 6 Week | 8 Week |
|---|---|---|---|---|---|---|---|---|
| Clarity | | clear | clear | clear | clear | clear | clear | clear |
| Color | | colorless | colorless | colorless | colorless | colorless | colorless | colorless |
| pH | | | 4.511 | 4.577 | 4.548 | 4.747 | 4.531 | 4.634 |
| Assay (% LC) | | 95-105% | 98.90% | 98.90% | 99.90% | 99.80% | 99.80% | 99.70% |
| Impurity A | 1.15 | <0.15% | BQL | BQL | BQL | BQL | BQL | BQL |
| Impurity B | 0.65 | <0.15% | ND | BQL | BQL | BQL | BQL | 0.05% |
| Impurity C | 0.58 | <0.15% | ND | ND | ND | BQL | BQL | BQL |
| Impurity D | 0.25 | <0.15% | BQL | BQL | BQL | BQL | BQL | BQL |
| Unknown | 0.41 | <0.10% | BQL | BQL | BQL | BQL | BQL | BQL |
| Impurities | 0.52 | <0.10% | BQL | BQL | BQL | BQL | BQL | BQL |
| | 0.62 | <0.10% | BQL | BQL | BQL | BQL | BQL | BQL |
| | 0.7 | <0.10% | BQL | BQL | BQL | BQL | BQL | BQL |
| | 0.8 | <0.10% | BQL | BQL | BQL | BQL | BQL | BQL |
| | 1.06 | <0.10% | ND | ND | ND | ND | BQL | ND |
| Total Impurity | | <0.50% | 0.00% | 0.00% | 0.00% | 0.00% | 0.00% | 0.05% |

TABLE 11

Stability of Formulation 1 to Freeze/Thaw Testing

| Formulation # 1 | Drug Substance | t = 0 | Cycle 1, −20° C. | Cycle 1, 25° C. | Cycle 2, −20° C. | Cycle 2, 25° C. | Cycle 3, −20° C. | Cycle 3, 25° C. |
|---|---|---|---|---|---|---|---|---|
| Date Observed: | | Jan. 16, 2015 | Jan. 18, 2015 | Jan. 20, 2015 | Jan. 22, 2015 | Jan. 24, 2015 | Jan. 26, 20415 | Jan. 28, 2015 |
| Physical appearance | clear | clear | clear | clear | clear | clear | clear | clear |
| Color | colorless | colorless | colorless | colorless | colorless | colorless | colorless | colorless |

Applicant determined that Formulation 1 was stable during each test by observation and chemical analysis. Further, Applicant determined that total and individual impurities were within acceptable limits.

In addition, Formulations 4A, 4B, 4D and 4E were subjected to stability testing. A summary of these results is below in "Table 12. Stability of Formulations 4A, 4B, 4D and 4E Subject to Freeze/Thaw Studies" and "Table 13. Stability of Formulations 4A, 4B, 4D and 4E Subject to 5° C."

TABLE 12

Stability of Formulations 4A, 4B, 4D and 4E Subject to Freeze/Thaw Studies

| # 4A | Drug Substance | t = 0 | Cycle 1, −20° C. | Cycle 1, 25° C. | Cycle 2, −20° C. | Cycle 2, 25° C. | Cycle 13, −20° C. | Cycle 13, 25° C. |
|---|---|---|---|---|---|---|---|---|
| Date Observed: | | Feb. 1, 2016 | Feb. 1, 2016 | Feb. 1, 2016 | Feb. 5, 2016 | Feb. 5, 2016 | Mar. 20, 2016 | Mar. 20, 2016 |
| Physical appearance | Clear | Clear | Clear | Clear | Clear | Clear | Clear | Clear |
| Color | Colorless | Colorless | Colorless | Colorless | Colorless | Colorless | Colorless | Colorless |

| # 4B | Drug Substance | t = 0 | Cycle 1, −20° C. | Cycle 1, 25° C. | Cycle 2, −20° C. | Cycle 2, 25° C. | Cycle 13, −20° C. | Cycle 13, 25° C. |
|---|---|---|---|---|---|---|---|---|
| Date Observed: | | Feb. 1, 2016 | Feb. 1, 2016 | Feb. 1, 2016 | Feb. 1, 2016 | Feb. 5, 2016 | Feb. 5, 2016 | Mar. 20, 2016 |
| Physical appearance | clear | Clear | Clear | Clear | Clear | Clear | Clear | Clear |
| Color | colorless | Colorless | Colorless | Colorless | Colorless | Colorless | Colorless | Colorless |

TABLE 12-continued

Stability of Formulations 4A, 4B, 4D and 4E Subject to Freeze/Thaw Studies

| # 4D | Drug Substance | t = 0 | Cycle 1, −20° C. | Cycle 1, 25° C. | Cycle 2, −20° C. | Cycle 2, 25° C. | Cycle 13, −20° C. | Cycle 13, 25° C. |
|---|---|---|---|---|---|---|---|---|
| Date Observed: | | Mar. 14, 2016 | Mar. 14, 2016 | Mar. 14, 2016 | Mar. 18, 2016 | Mar. 18, 2016 | Mar. 22, 2016 | Mar. 22, 2016 |
| Physical appearance | clear | Clear | Solidified | Clear | Solidified | Clear | Solidified | Clear |
| Color | colorless | Colorless | White | Colorless | White | Colorless | White | Colorless |

| # 4E | Drug Substance | t = 0 | Cycle 1, −20° C. | Cycle 1, 25° C. | Cycle 2, −20° C. | Cycle 2, 25° C. | Cycle 13, −20° C. | Cycle 13, 25° C. |
|---|---|---|---|---|---|---|---|---|
| Date Observed: | | Mar. 14, 2016 | Mar. 14, 2016 | Mar. 14, 2016 | Mar. 18, 2016 | Mar. 18, 2016 | Mar. 22, 2016 | Mar. 22, 2016 |
| Physical appearance | clear | Clear | Solidified | Clear | Solidified | Clear | Solidified | Clear |
| Color | colorless | Colorless | White | Colorless | White | Colorless | White | Colorless |

TABLE 13

Stability of Formulations 4A, 4B, 4D and 4E Subject to 5° C.

| # 4A | t = 0 | Day 1 | Day 8 | Day 50 |
|---|---|---|---|---|
| Date Observed: | Feb. 1, 2016 | Feb. 2, 2016 | Feb. 9, 2016 | Mar. 22, 2016 |
| Physical appearance | Clear | Crystals | Crystals | Crystals |
| Color | Colorless | Colorless | Colorless | Colorless |
| # 4B | t = 0 | Day 1 | Day 8 | Day 50 |
| Date Observed: | Feb. 1, 2016 | Feb. 2, 2016 | Feb. 9, 2016 | Mar. 22, 2016 |
| Physical appearance | Clear | Clear | Clear | Clear |
| Color | Colorless | Colorless | Colorless | Colorless |
| # 4D | t = 0 | Day 1 | Day 8 | |
| Date Observed: | Mar. 14, 2016 | Mar. 15, 2016 | Mar. 23, 2016 | |
| Physical appearance | Clear | Clear | Clear | |
| Color | Colorless | Colorless | Colorless | |
| # 4E | t = 0 | Day 1 | Day 8 | |
| Date Observed: | Mar. 14, 2016 | Mar. 15, 2016 | Mar. 23, 2016 | |
| Physical appearance | Clear | Clear | Clear | |
| Color | Colorless | Colorless | Colorless | |

As seen in Tables 12 and 13, no crystals developed and the formulations remained stable despite the harsh conditions.

Example 6

In order to determine the spray profile of Formulation 1, it was subjected to standardized droplet testing. A challenge of creating a sildenafil sublingual spray formulation is that it must be capable of producing spray droplets that are over 10 microns in diameter. Spray droplets 10 microns or smaller could be inhaled into the lungs. The optimal particle size for sublingual spray droplets is from 20 to about 200 microns in diameter. It is desirable for the formulation to have droplet sizes near 20 because this increases the surface area and increased surface area exposure is one factor that contributes to a high bioavailability. Sublingual formulations should be able to maintain a consistent droplet size throughout its shelf life.

Droplet analysis was conducted using standard laser analysis procedures known by those of skill in the art. Droplet size distribution (Dv10, Dv50, Dv90, and Span were tested at two distances, 3 cm and 6 cm). Dv10 refers to droplet size for which 10% of the total volume is obtained; Dv50 refers to droplet size for which 50% of the total volume is obtained; Dv90 refers to droplet size for which 90% of the total volume is obtained; Span refers to distribution span (Dv90−Dv10)/Dv50; % RSD refers to the percent relative standard deviation. The results of these tests can be seen below in Tables 14 to 19. Applicant found during testing that formulations of the present invention yielded desirable droplet sizes for sublingual administration. The testing also revealed that the formulation dose remains consistent when administered with a spray pump.

TABLE 14

Spray Profile of Sildenafil Spray Formulation 1, Particle Size at 3 cm

| Formulation #1 | DV(10) | DV(50) | DV(90) | %<10μ | D(4, 3) | Span |
|---|---|---|---|---|---|---|
| Actuation 1 | 19.8 | 55.84 | 342.5 | 1.205 | 121.4 | 5.78 |
| Actuation 2 | 20.17 | 51.61 | 263.1 | 0.2293 | 105.5 | 4.707 |
| Actuation 3 | 20.39 | 72.27 | 453.8 | 0.269 | 161.8 | 5.998 |
| Average | 20.12 | 59.91 | 353.13 | 0.57 | 129.57 | 5.50 |

TABLE 15

Spray Profile of Sildenafil Spray Formulation 1, Particle Size at 6 cm

| Formulation #1 | DV(10) | DV(50) | DV(90) | %<10μ | D(4, 3) | Span |
|---|---|---|---|---|---|---|
| Actuation 1 | 24.57 | 55.86 | 487.2 | 1.133 | 151.2 | 8.282 |
| Actuation 2 | 28.29 | 65.85 | 509.9 | 0 | 171.1 | 7.314 |
| Actuation 3 | 25.4 | 54.14 | 423.1 | 1.263 | 130.9 | 7.346 |
| Average | 26.09 | 58.62 | 473.40 | 0.80 | 151.07 | 7.65 |

TABLE 16

Spray Profile of Sildenafil Spray Formulation 1, Spray Pattern at 3 cm

| Formulation #1 | Dmin (mm) | Dmax (mm) | Ovality Ratio |
|---|---|---|---|
| Actuation 1 | 20 | 26.4 | 1.32 |
| Actuation 2 | 18.4 | 24.7 | 1.346 |
| Actuation 3 | 18 | 25.7 | 1.433 |
| Average | 18.80 | 25.60 | 1.37 |

TABLE 17

Spray Profile of Sildenafil Spray Formulation 1, Spray Pattern at 6 cm

| Formulation #1 | Dmin (mm) | Dmax (mm) | Ovality Ratio |
|---|---|---|---|
| Actuation 1 | 14.7 | 28.5 | 1.931 |
| Actuation 2 | 20.1 | 28.8 | 1.433 |
| Actuation 3 | 15.5 | 21.7 | 1.401 |
| Average | 16.77 | 26.33 | 1.59 |

TABLE 18

Spray Profile of Sildenafil Spray Formulation 1, Plume geometry data at 3 cm

| Formulation #1 | Width (mm) | Angle (°) |
|---|---|---|
| Actuation 1 | 25.3 | 45.4 |
| Actuation 2 | 16.5 | 30.4 |
| Actuation 3 | 16.8 | 31.2 |
| Average | 19.53 | 35.67 |

TABLE 19

Spray Profile of Sildenafil Spray Formulation 1, Plume geometry data at 6 cm

| Formulation #1 | Width (mm) | Angle (°) |
|---|---|---|
| Actuation 1 | 31 | 28.4 |
| Actuation 2 | 29.5 | 27.7 |
| Actuation 3 | 16.8 | 15.7 |
| Average | 25.77 | 23.93 |

As can be seen in Tables 14 to 19, Formulation 1 of the present invention provided excellent plume geometry and spray patterns.

Example 7

In Vitro Permeation of Formulations 4A-4F and 4H

The permeation characteristics of sildenafil formulations were studied using porcine buccal tissue. The porcine buccal model exhibits in vivo like morphological characteristics. Results of the in vitro permeation study can be seen in "Table 20. In-Vitro Permeation of Formulations 4A-4F and 4H through Porcine Buccal Epithelium" and in FIG. 1.

TABLE 20

In Vitro Permeation of Formulations 4A-4F and 4H through Porcine Buccal Epithelium

| Formulation ID | Mean Flux | SEM | Mean P | SEM |
|---|---|---|---|---|
| 4A | 0.69 | 0.147 | 7.20E-08 | 1.54E-08 |
| 4B | 0.47 | 0.16 | 4.92E-08 | 1.66E-08 |
| 4C | 16.79 | 3.095 | 1.75E-06 | 3.22E-07 |
| 4D | 14.06 | 1.716 | 2.93E-06 | 3.58E-07 |
| 4E | 13.59 | 1.427 | 1.42E-06 | 1.49E-07 |
| 4F | 18.78 | 0.936 | 3.91E-06 | 1.95E-07 |
| 4H | 15.06 | 2.564 | 1.57E-06 | 2.67E-07 |

Figure 1:
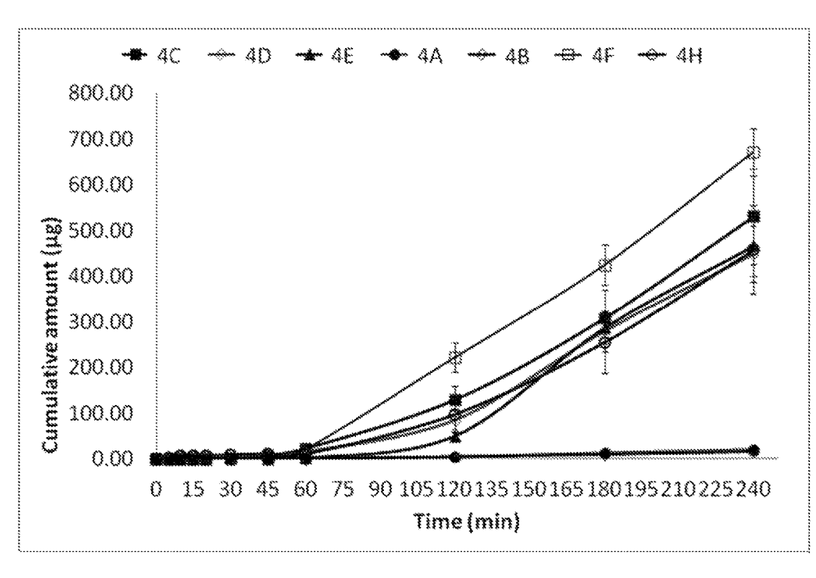
FIG. 1. A Line-plot of Cumulative Permeation of Sildenafil through Porcine Buccal Epithelium.

As seen in Table 20 and FIG. 1, the addition of caprylic acid to formulations containing either propylene glycol or glycerol vastly improves the permeation of sildenafil through porcine buccal epithelium. Compare Formulation 4A to 4E (propylene glycol) where Mean Flux increased 20 fold and Formulation 4B to 4H (glycerol) where Mean Flux increased 32 fold.

We claim:

1. A sublingual spray formulation comprising:
   a. from about 5% w/w to about 35% w/w sildenafil or a salt thereof;
   b. from about 0.1% w/w to about 60% w/w of at least one pharmacologically acceptable polar solvent selected from the group consisting of purified water, ethanol, and polyethylene glycol 400;
   c. an excipient selected from about 0.1% w/w to about 50% w/w glycerol, from about 0.1% w/w to about 50% w/w propylene glycol and a combination thereof;
   d. from about 0.1% w/w to about 60% w/w of at least one acid selected from the group consisting of an inorganic acid and an organic acid; and
   e. a permeation enhancer comprising caprylic acid,
   wherein the permeation enhancer enhances sublingual delivery of sildenafil or a salt thereof and wherein % w/w is of the total formulation.

2. The formulation of claim 1 wherein the acid is diluted hydrochloric acid.

3. The formulation of claim 1 wherein the excipient is from about 5% w/w to about 30% w/w glycerol.

4. The formulation of claim 1 comprising from about 0.1% w/w to about 50% w/w water.

5. The formulation of claim 1 comprising from about 10% w/w to about 60% w/w ethanol.

6. The formulation of claim 1 wherein the excipient is from about 5% w/w to about 30% w/w propylene glycol.

7. The formulation of claim 1 wherein the formulation is propellant free.

8. The formulation of claim 1 wherein the sildenafil is a pharmaceutically acceptable salt selected from the group consisting of citrate, hydrochloride, halide, sulfate, phosphate, acetate, maleate, succinate, ascorbate, carbonate, mesylate and lactate.

9. The formulation of claim 1 further comprising an antioxidant and/or stabilizer, sweetener, sweetness enhancer, pH modifier, flavoring agent, permeation enhancer, preservative, or a combination thereof.

10. The formulation of claim 9 comprising an antioxidant and/or stabilizer selected from the group consisting of ascorbyl palmitate, ascorbic acid, alpha tocopherol, butylated hydroxytoluene, buthylated hydroxyanisole, cysteine HCl, citric acid, ethylenediamine tetra acetic acid (EDTA), methionine, sodium citrate, sodium ascorbate, sodium thiosulfate, sodium metabisulfite, sodium bisulfate, propyl gallate, glutathione and thioglycerol.

11. The formulation of claim 9 wherein the permeation enhancer further comprises a second compound selected from the group consisting of menthol, limonene, carvone, methyl chitosan, polysorbates, sodium lauryl sulfate, glyceryl oleate, caproic acid, enanthic acid, pelargonic acid, capric acid, undecylenic acid, lauric acid, myristic acid, palmitic acid, oleic acid, stearic acid, linoleic acid, arachidonic acid, benzethonium chloride, benzethonium bromide, benzalkonium chloride (BKC), cetylpyridium chloride, edetate disodium dihydrate, sodium desoxycholate, sodium deoxyglycolate, sodium glycocholate, sodium caprate, sodium taurocholate, sodium hydroxybenzoyal amino caprylate, dodecyl dimethyl aminopropionate, L-lysine, glycerol oleate, glyceryl monostearate, citric acid, peppermint oil and a combination thereof.

12. The formulation of claim 11, wherein the permeation enhancer comprises menthol as the second compound.

13. The formulation of claim 1, wherein the caprylic acid is at a concentration from about 0.1% w/w to about 20% w/w.

14. The formulation of claim 13, wherein the caprylic acid is at a concentration from about 0.1% w/w to about 5% w/w.

15. A propellant free sublingual spray formulation comprising:
   a. from about 5% w/w to about 20% w/w sildenafil or a salt thereof;
   b. from about 35% w/w to about 55% w/w ethanol;
   c. from about 1% w/w to about 30% w/w water;
   d. an excipient selected from the group consisting of from about 5% w/w to about 30% w/w glycerol, from about 5% w/w to about 30% w/w propylene glycol, and from about 5% w/w to about 30% w/w polyethylene glycol 400; and
   e. from about 0.1% w/w to about 60% w/w diluted hydrochloric acid; and
   f. a permeation enhancer comprising caprylic acid,
   wherein % w/w is of the total formulation.

16. A propellant free sublingual spray formulation comprising:
   a. about 8% w/w sildenafil or a salt thereof;
   b. about 40% w/w ethanol;
   c. about 10% w/w glycerol;
   c. about 26% w/w water;
   d. about 12% w/w diluted hydrochloric acid; and
   e. a permeation enhancer comprising 0.5% w/w menthol and 2% w/w caprylic acid,
   wherein % w/w is of the total formulation.

17. A method of treating sexual dysfunction in men comprising administering the formulation of claim 1 to a patient in need thereof.

18. The method of claim 17, wherein the spray pumps deliver about 50 to 400 of the formulation of claim 1 under the tongue.

19. A method of treating pulmonary arterial hypertension in a human comprising administering the formulation of claim 1 to a patient in need thereof.

* * * * *